US008845556B1

(12) United States Patent
Schickler et al.

(10) Patent No.: US 8,845,556 B1
(45) Date of Patent: Sep. 30, 2014

(54) METHOD AND APPARATUS FOR BODY BALANCE AND ALIGNMENT CORRECTION AND MEASUREMENT

(76) Inventors: Pamela Schickler, Rochester, NY (US); John F. Schickler, Rochester, NY (US)

( * ) Notice: Subject to any disclaimer, the term of this patent is extended or adjusted under 35 U.S.C. 154(b) by 101 days.

(21) Appl. No.: 12/661,105

(22) Filed: Mar. 8, 2010

Related U.S. Application Data

(60) Provisional application No. 61/209,532, filed on Mar. 6, 2009, provisional application No. 61/276,309, filed on Sep. 10, 2009.

(51) Int. Cl.
*A61B 5/117* (2006.01)
*A61B 5/103* (2006.01)
*G08B 23/00* (2006.01)

(52) U.S. Cl.
USPC .................................. 600/595; 340/573.7

(58) Field of Classification Search
USPC ............... 600/587, 595, 592, 594; 702/188, 702/182–185; 382/154, 276; 473/131; 463/36; 340/572.1, 7.2, 573.1, 573.7
See application file for complete search history.

(56) References Cited

U.S. PATENT DOCUMENTS

| | | | | |
|---|---|---|---|---|
| 6,010,465 | A * | 1/2000 | Nashner | 600/595 |
| 7,299,159 | B2 * | 11/2007 | Nanikashvili | 702/188 |
| 2002/0009222 | A1 * | 1/2002 | McGibbon et al. | 382/154 |
| 2006/0025229 | A1 * | 2/2006 | Mahajan et al. | 473/131 |
| 2009/0322533 | A1 * | 12/2009 | Bomba et al. | 340/572.1 |

OTHER PUBLICATIONS

Foster, Jordana, Low-Tech Balance Training Decreases Ankle Sprain Risk, Published in Jul. 2007 issue of BioMechanics.*

* cited by examiner

Primary Examiner — Brian Szmal
(74) Attorney, Agent, or Firm — Steven R. Scott

(57) ABSTRACT

This invention pertains generally to non-invasive methods and apparatus for analyzing and improving human balance. More particularly, this invention describes a human balance analysis and improvement apparatus and method that involves the use of separate and synergistically integrated and combined means for analyzing and producing perfect core body alignment and balance: an alignment indicator, sway measurement apparatus, and foot force measurement and force centering apparatus. Data received from the aforesaid devices or various combinations thereof is then integrated and displayed by appropriate software and/or display apparatus for use in perfecting, analyzing and/or correcting human balance. The alignment and sway measurement apparatus of the invention is preferably subject based upon video motion capture technology. The foot force measurement and force centering apparatus is preferably based upon a pair of segmented force plates with underlying sensors capable of registering differences in distribution of weight on different parts of the segments.

20 Claims, 19 Drawing Sheets

ΔP = CHANGES IN BODY POSITIONS RELATIVE TO CHANGES IN CENTER OF FORCE

ΔE = ENERGY (POWER) REQUIRED TO CORRECT ΔP f = FREQUENCY OF ΔP

V = COF VS. Z PERFECT

COF = CENTER OF FOOT FORCE

METHOD AND APPARATUS FOR BODY BALANCE AND ALIGNMENT CORRECTION AND MEASUREMENT

CROSS-REFERENCE TO RELATED APPLICATIONS

This application claims an invention which was disclosed in a provisional application filed Mar. 6, 2009, Ser. No. 61/209,532, entitled "Method and Apparatus for Body Balance and Alignment Correction and Measurement", and a provisional application filed Sep. 10, 2009, Ser. No. 61/276,309, entitled "Method and Apparatus for Body Balance and Alignment Correction and Measurement". The benefit under 35 USC §119(e) of these United States provisional applications is hereby claimed, and the aforementioned applications are hereby incorporated herein by reference.

BACKGROUND AND SUMMARY

This invention pertains generally to non-invasive methods and apparatus for analyzing and improving human balance. More particularly, this invention describes a human balance analysis and improvement apparatus and method that involves the use of separate and synergistically integrated and combined means for analyzing and producing perfect core body alignment and balance: a torso alignment indicator and sway measurement apparatus and system, a foot force measurement and force centering apparatus and system, balance information display apparatus and system, apparatus and methods for calibration of the said apparatus and system, and processing apparatus and systems for combining, displaying and facilitating the operations of the foregoing. In initial non-preferred embodiments of the invention, the alignment indicator apparatus and system included laser alignment apparatus and sway measurement apparatus based on a subject mounted accelerometer or infrared technology. In the preferred embodiment, the aforesaid functions are performed using motion capture video technology. The foot force measurement and force centering apparatus and system may use available technology such as a MATSCAN® mat or use a sensor mounted rigid balance board, but is preferably based upon the force plates of the invention. Data received from the aforesaid devices or various combinations thereof is then integrated and displayed by appropriate software and/or display apparatus for use in perfecting, analyzing and/or correcting human balance. Calibration is accomplished by a unique equilibrium measurement apparatus (the Balance Testing Device of the invention) and a method for using the apparatus which provide an objective means for evaluating the data obtained via the aforesaid devices and systems to arrive at objective balance and likelihood of falling scores and measurements.

The science of human kinesiology defines numerous factors that influence a person's sense of balance and ability to perform movement with confidence. Those factors are both physical and mental, derived from sensory inputs to the brain, including signals from the inner ear, eyesight and feet. In addition, many professionals associated with improvement in human kinetics acknowledge the significance of balance in achieving improvement in their subjects. Coaches, dance instructors, therapists, trainers, doctors include those who advocate balance training as a key factor in development of improved kinetic capability. Finally, the measurement and analysis of balance in the human body, both static and dynamic, is of increasing importance as the population ages.

It is estimated that the cost of falls in the U.S. alone is responsible for 17 billion dollars per year.

The array of equipment used by professionals to develop improved balance in their subjects includes numerous sensors and training devices which either attach to the person or act to support the person and let a professional analyze what the person's performance appears to be. Historically, the measurements of balance have focused upon force measurements at the feet or sway of the body core in order to achieve neuromuscular reduction. In some cases, sway is deduced from measurements of height, body mass index and foot force variation. In others, sway is analyzed using accelerometers with no reference to foot force.

However, with all of the attention placed upon improving balance, there is no simple objective measurement of "perfect balance" which can serve as a "benchmark" for use in analysis and correction of balance issues and to which a person can aspire. That is, all of the current measurement devices define outputs of performance but do not correlate those outputs with a set of measurable standards for various movements to define balance and to provide feedback on how it may be attained. The instant invention provides the means to establish those standards and show a subject what must be done to meet them while using the device. The significance of such a device is that it can be applied by all who seek to improve human kinetics in many different venues with any number of different subjects of varying capability, including the elderly, the disabled, the injured and the healthy.

In addition, it correlates an array of measuring equipment into a single measurement apparatus, system, method and set of standards that can be viewed in both static and dynamic formats at relatively low cost. It does this by creating a means of directly measuring alignment of the body core with the feet while directly measuring both sway and foot forces and integrating the three variables into one measurement system. Further, the apparatus for calibration of the balance measurement devices and systems described in order to arrive at objective standards and measurements for balance and likelihood of falling can also be used to help calibrate and objectify the less perfect measurements obtained using existing systems.

In its preferred embodiments, the system of the invention uses two force plates and two video cameras joined in a fixed framework and linked to a data processing device such as a personal computer. A person being measured dons an adjustable vest containing sensors on the back which can be moved to specific body points for best analysis of balance. The subject mounts the force plates and performs simple maneuvers which are captured in seconds by the computer operated by a therapist. The slightest variation in body movements and foot force distribution are detected. Each maneuver is 15 seconds or less with eyes open or closed. On video display provided by the system (which will typically be accessed via an associated personal computer monitor) the therapist sees every aspect of the subject's performance for the entire body, including sway, center of force, frequency of movement and posture. These are automatically recorded in millisecond increments and can be analyzed for each body segment. The software automatically integrates the feet with the upper body. However, the key output of the software is the scoring system.

Every measurement provides a completely objective score which has been correlated with exact determination of the power required to correct movement and maintain balance, as well as predict risk of fall. The best score is preset to 100. The system detects in seconds any deviation from 100 and provides an overall score at the end of each maneuver. The subject's scores are recorded and tracked in the software to display progress. Next, the therapist selects therapeutic protocols from an electronic library in the software. They can be customized by the therapist and copied or emailed to the subject. Each is saved in the person's record. Finally, a person can obtain training to improve balance right on the equipment provided. Various exercises are electronically measured and the results viewed by the subject and/or therapist in a dynamic mode as the therapist advises the subject on the proper movement and determines necessary changes.

BRIEF DESCRIPTION OF THE DRAWINGS

FIG. 12 is a first exemplary screen shot provided in accordance with the teaching and system of the invention, providing output based on and illustrating individual foot forces as well as displaying upper body movement via video capture of the luminous pods on the back of a vest worn by the subject.

FIG. 13 is a second exemplary screen shot provided in accordance with the teaching and system of the invention, illustrating the patient record and indicating risk of fall.

FIG. 14 is a third exemplary screen shot provided in accordance with the teaching and system of the invention, illustrating a selection of therapeutic protocols that can be copied and emailed to the patient.

DESCRIPTION

Figure 1:
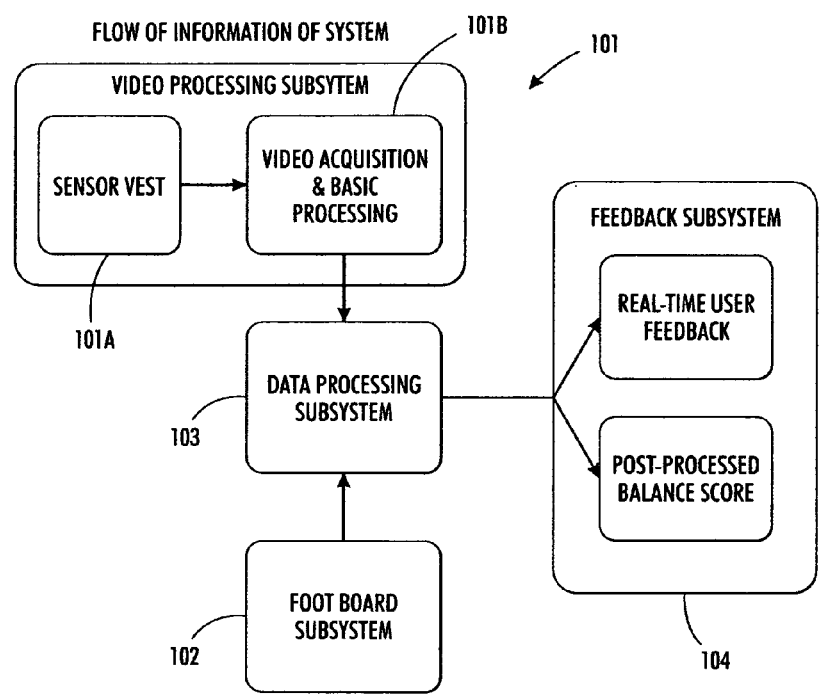
FIG. 1 provides a schematic illustration and overview of the systems/subsystems of the preferred embodiment of the invention.

In its preferred embodiments, the invention is generally comprised of four major components: (1) Apparatus and systems related to measuring and/or tracking core alignment and/or a subject's upper body position/posture 101; (2) apparatus and systems related to measuring and/or tracking the distribution of foot force via the subject's feet 102; (3) apparatus and systems for data processing receiving data from the prior two systems and any associated apparatus and generating information on and tracking the subject's core alignment and/or upper body position/posture, distribution of weight at the subject's feet, and/or center of force at the subject's feet 103; (4) a preferred mode of measuring, processing, evaluating, interpreting and/or scoring balance and performance based on the foregoing 200; and (5) apparatus and systems related to providing feedback based on the foregoing 104, which systems and apparatus receive said information from the data processing apparatus and systems and compile/display it in a meaningful manner for the subject and/or a monitor or therapist. In addition, apparatus (such as the testing device described below) that allow the development of an objective scale against which the subject's performance can be measured, can also be seen as playing an important part in the inventive concept and its implementation.

In the process of arriving at the aforesaid apparatus and system, numerous alternative means for accomplishing the foregoing were developed, as more fully described in the previously filed provisionals, which have been incorporated herein by reference. As more fully explored in these provisionals, foot force distribution can be measured using a balance board or foot force measurement mat, but is preferably measured via a force plate (or plates) 100 for measurement of subject weight distribution (i.e., force) conveyed via the subject's feet as means of support for the subject as a dynamic system. Likewise, various modes for determining upper body position, movement and alignment; providing visual feedback; and/or analyzing results have been used in various prior embodiments and are described in the referenced provisionals. However, the preferred embodiment described herein has proven to be superior to prior embodiments and is the basis for the description provided (even though many of the teachings and practices of prior embodiments are incorporated therein).

An overview of the organization of the system of the invention is provided in FIG. 1, where it can be seen that the preferred embodiment of the human balance analysis and improvement apparatus of the invention is based on two basic sources for data input: a video processing subsystem 101 gathering video data related to a subject's upper body position; and a foot force analysis subsystem 102 gathering force distribution data related to distribution of foot force via the subject's feet. A data processing subsystem 103 receives the video data from the video processing system 101 and processes this data to generate information on the subject's center of mass, core alignment, movement, and other factors hereinafter described. The data processing subsystem 103 also receives the force distribution data from the foot force analysis system 102 and processes this data to generate information on distribution of subject weight at the subject's feet and/or a center of force at the subject's feet. The information generated by the data processing subsystem 103 is displayed via a feedback system 104 which receives said information from the data processing system 103 and displays it in a meaningful manner for the subject and/or a monitor or therapist as also described below.

Figure 2:
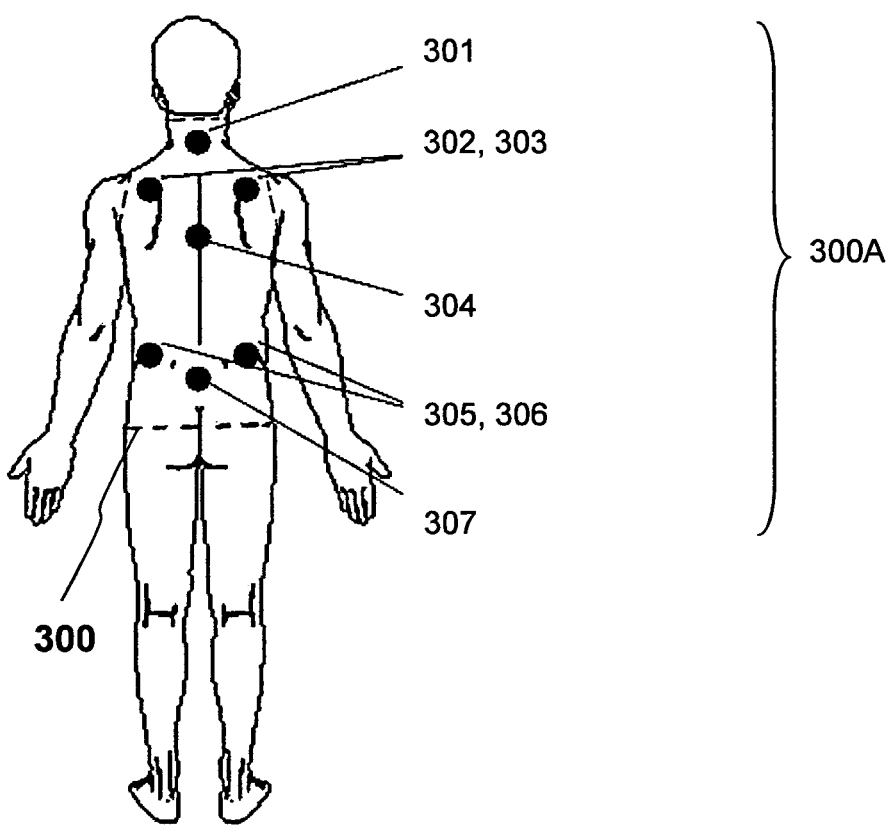
FIG. 2 provides a schematic diagram of a human body illustrating preferred placement of motion capture targets or "pods".

The video processing subsystem 101, which in the preferred embodiments (as previously noted) is founded in motion capture technology, is based on subject mounted posture tracking apparatus 101A and video acquisition apparatus 101B. These roles can advantageously be filled by an adjustable vest 300 with motion capture targets 301, 302, 303, 304, 305, 306, 307 mounted thereon (serving as the subject mounted posture tracking apparatus 101A of video processing subsystem 101), and a pair of video cameras 103A, 103B mounted so as to monitor the subject from right angles (serving as the said video acquisition apparatus 101B). Targets 301, 302, 303, 304, 305, 306, 307 (indicated generally by bracket 300A) are positioned for ease in determining and identify the subject's core as well as to monitor subject twist, sway, and bending. For this purpose, the points illustrated in FIG. 2 have been generally found to represent those preferred for placement of motion capture targets (or "pods") 301 (C7 spinous process), 302 (left superior angle of scapula), 303 (right superior angle of scapula), 304 (T7 spinous process), 305 (left iliac crest of pelvis), 306 (right iliac crest of pelvis), 307 (L5 spinous process), though these can be adjusted as necessary in particular cases by the therapist. (For adjustment purposes, Velcro® structures or other means well known in the mechanical arts can be used).

Figure 3:
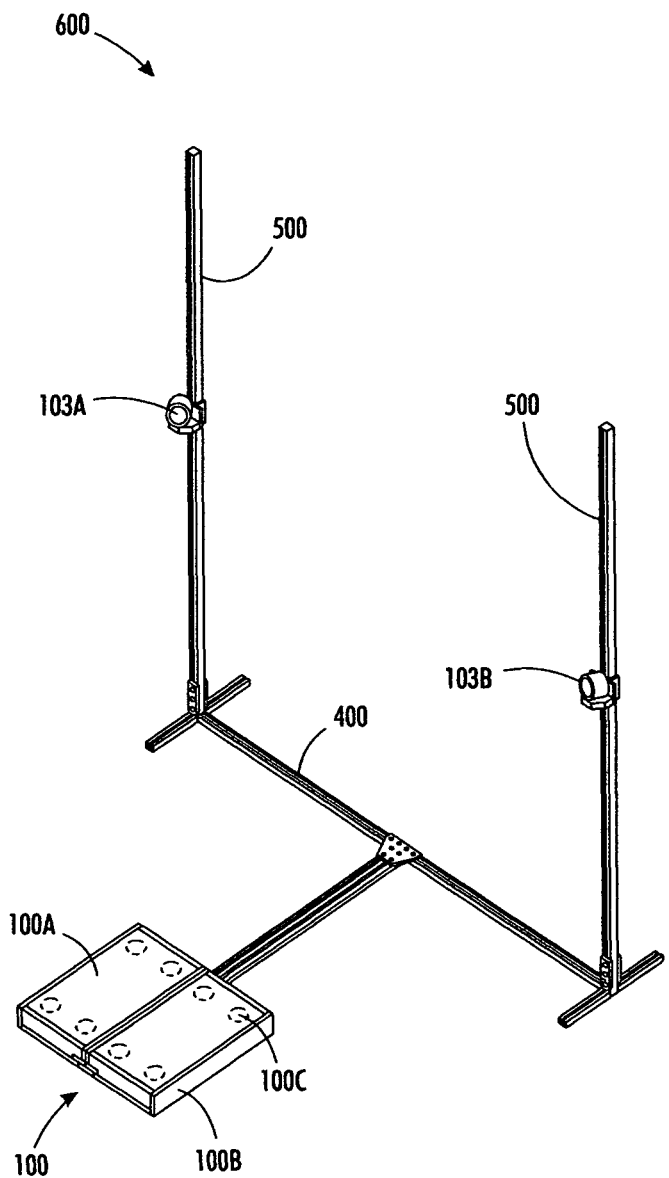
FIG. 3 provides a perspective view of an exemplary structure, layout and hardware for implementing the video acquisition and foot force analysis systems of the preferred embodiment of the invention.
Figure 4A:
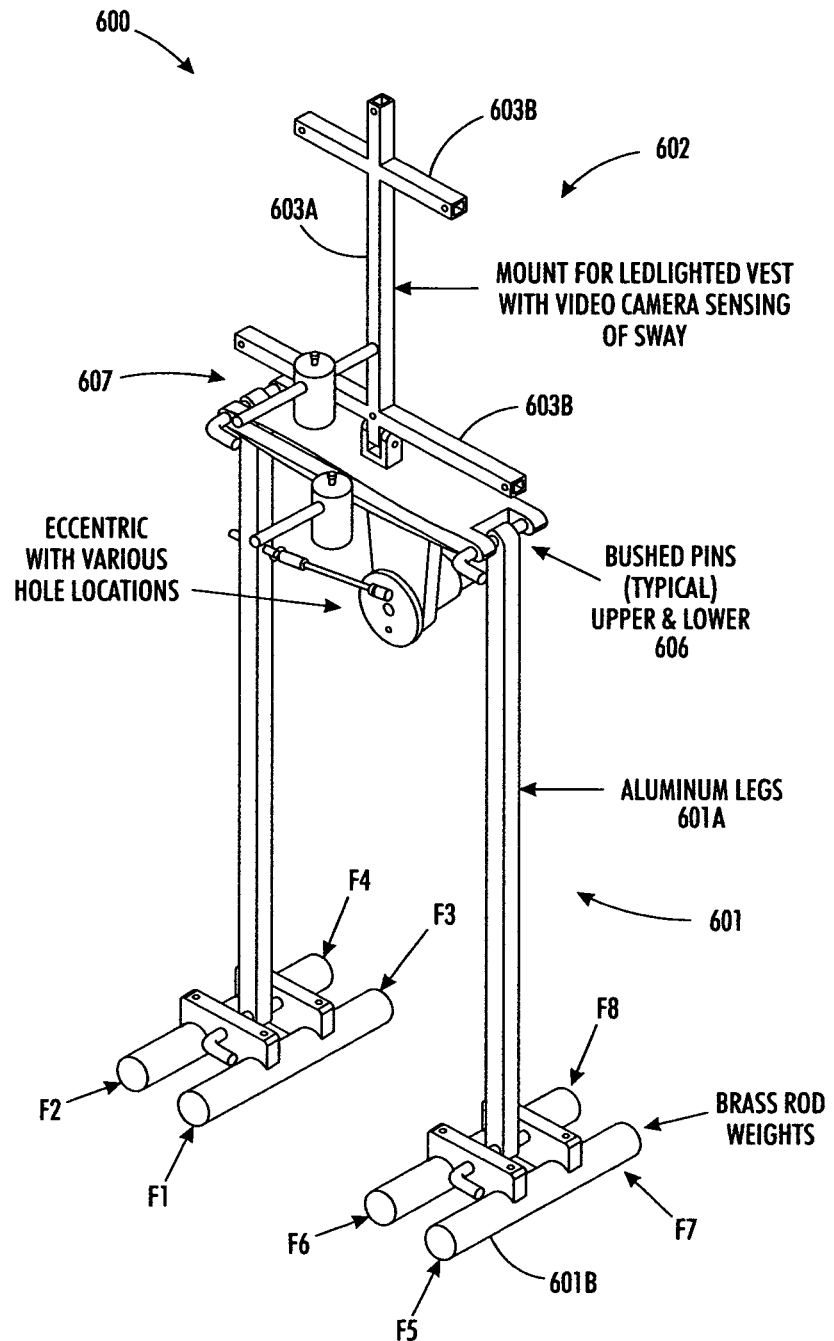
FIG. 4A provides a perspective view of a first embodiment of the Balance Testing Device of the invention.
Figure 4B:
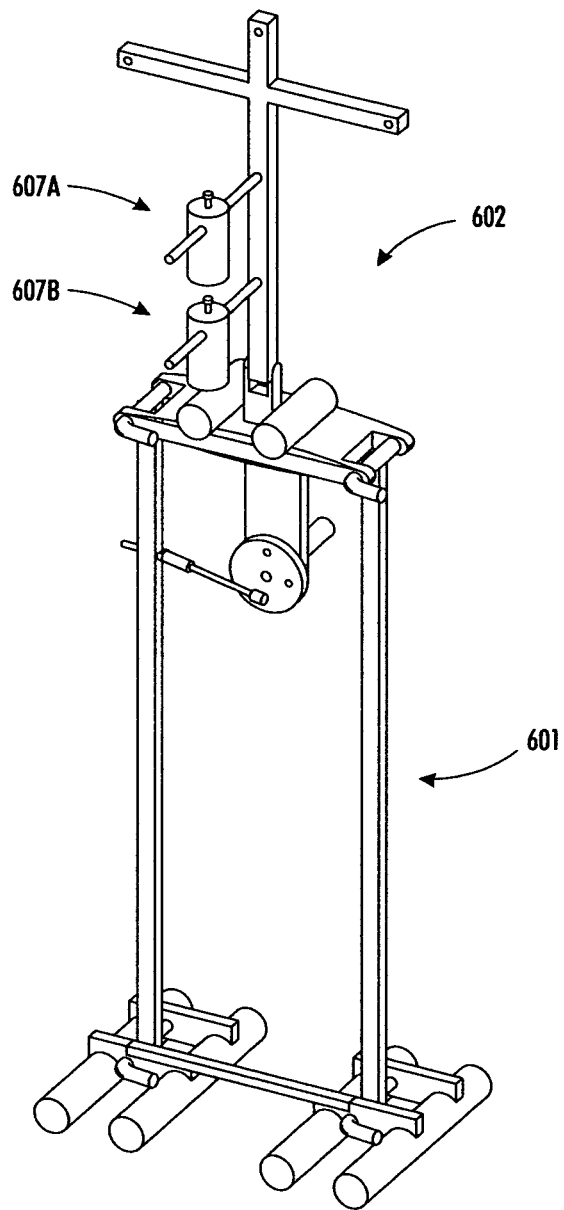
FIG. 4B provides a perspective view of a second embodiment of the Balance Testing Device of the invention.
Figure 5:
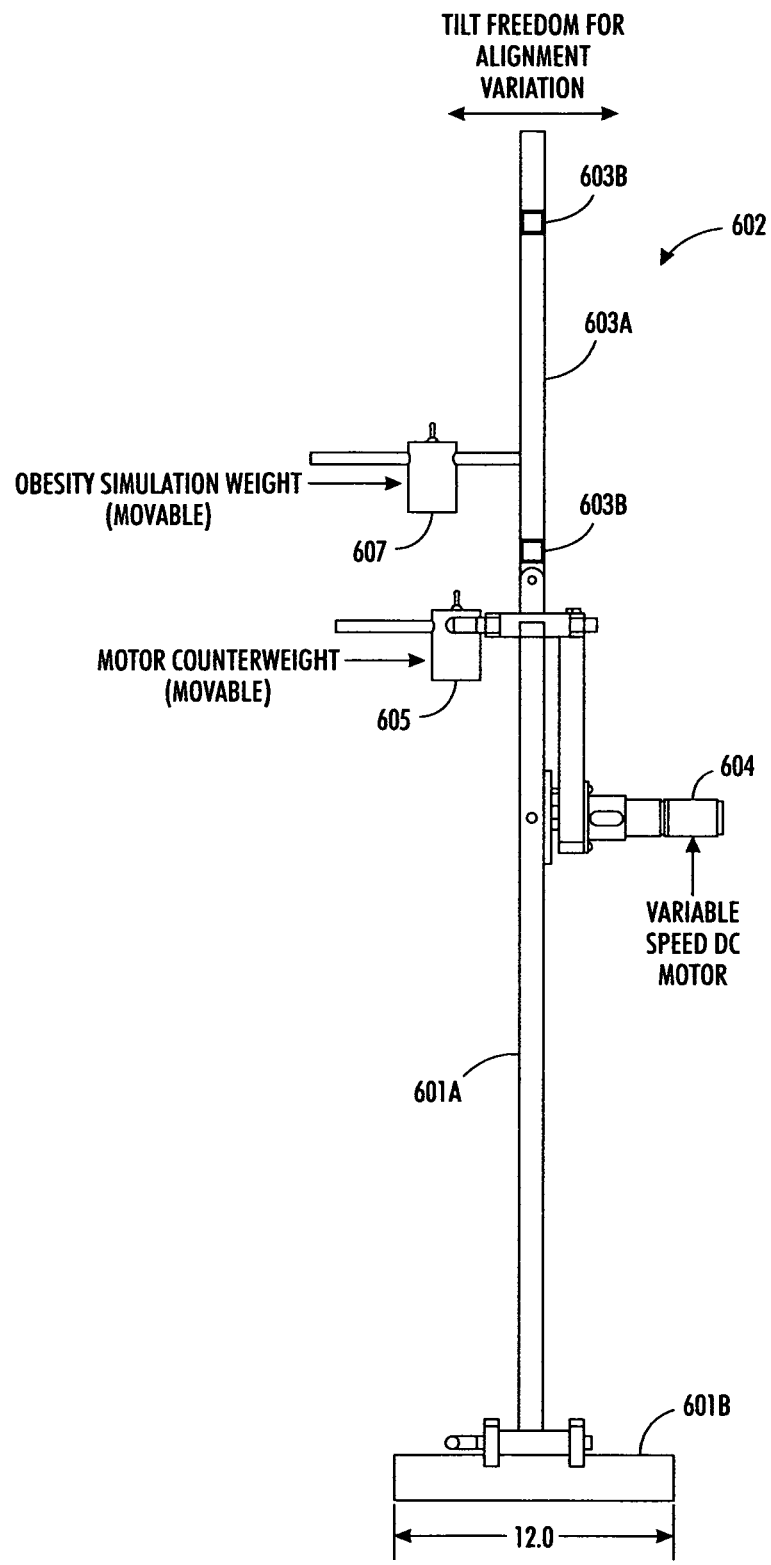
FIG. 5 provides a schematic side view of the first embodiment of the Balance Testing Device of the invention.
Figure 6:
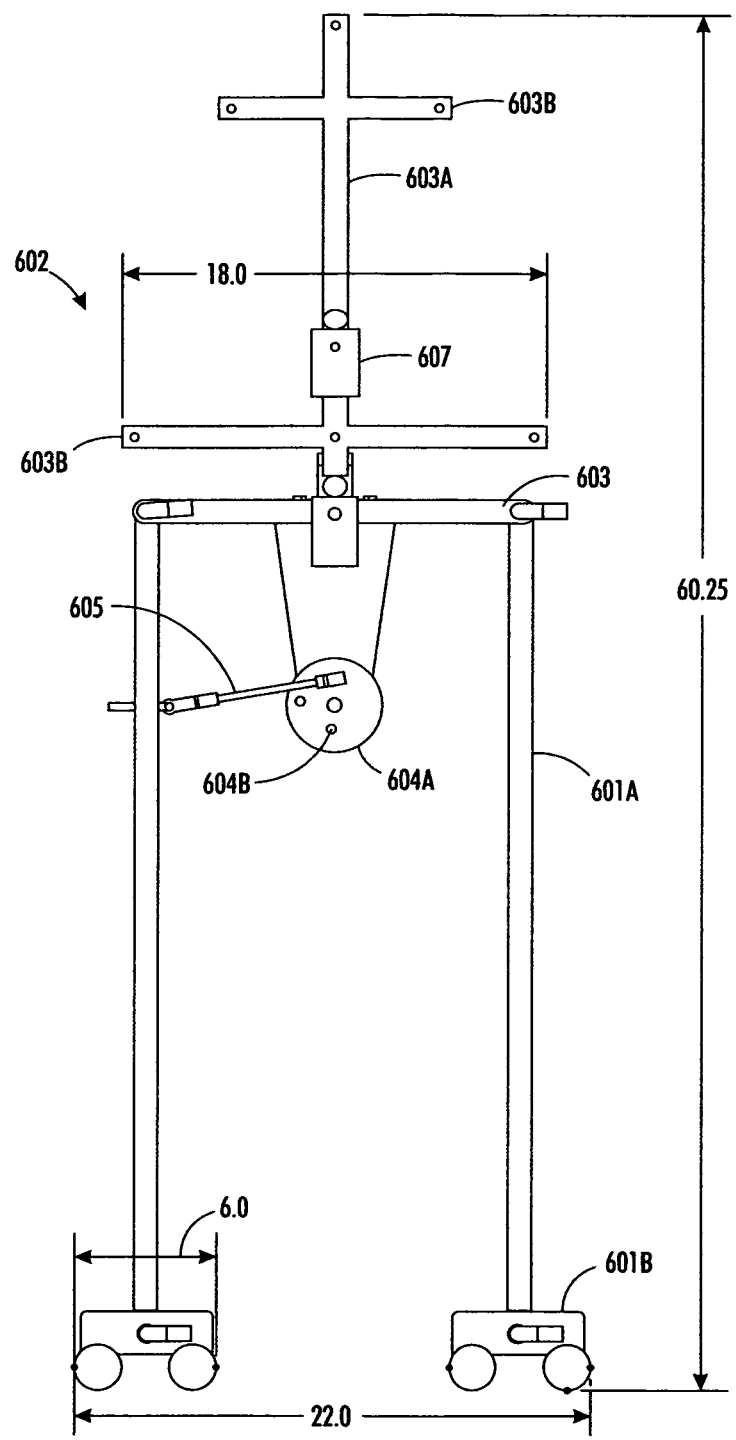
FIG. 6 provides a schematic frontal view of the first embodiment of the Balance Testing Device of the invention.
Figure 7:
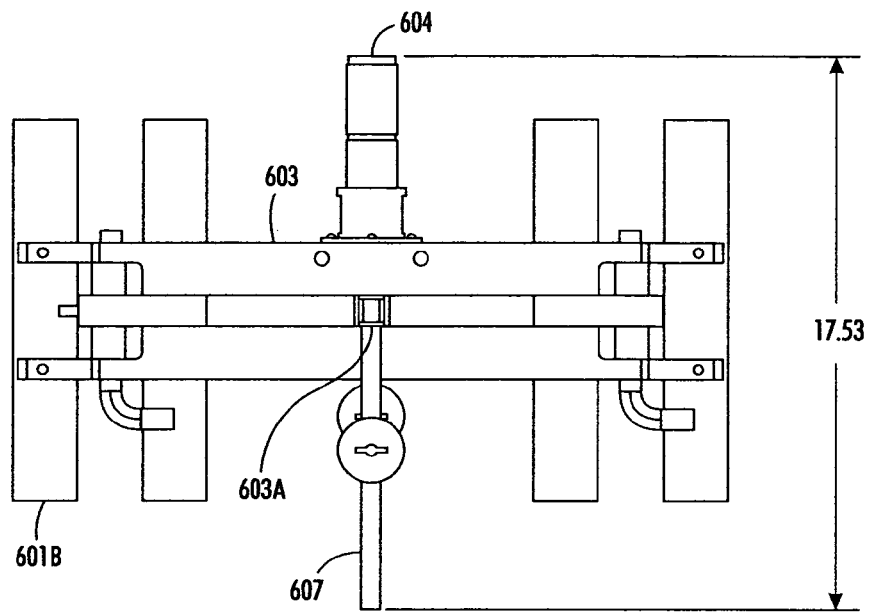
FIG. 7 provides a schematic top view of the first embodiment of the Balance Testing Device of the invention.

Still further information related to the implementation of the aforesaid system can be derived from FIG. 3, illustrating a preferred structure, layout and hardware for implementing the video acquisition and processing subsystem 101B and the foot force analysis system 102. As will be seen from this illustration, motion capture cameras 103A, 103B comprising video acquisition and processing subsystem 101B are held in spaced relationship to the foot force plate sections 100A, 100B comprising foot force analysis subsystem 102 by horizontal frame members 400 and vertical frame members 500. Vertical frame members 500 allow vertical adjustment of the motion capture cameras 103A, 103B as necessary to properly capture the sensor vest 101A of the subject in their field of view. Likewise, horizontal frame members 500 allow readjustment of the distance and relative placement of left foot section 100A and right foot section 100B as necessary, particularly as may be necessary to stagger said sections 100A, 100B for analysis of a subject's balance in relation to gait and staggered/spread foot placement. High quality computer web cameras are suitable for use as motion capture cameras 103A, 103B. The focal range of the cameras 103A, 103B is also important, with proximity to the subject guarantying maximum accuracy. However, cameras 103A, 103B should not be placed so close as to compromise their field of view.

As illustrated in FIG. 3, the force plates 100 of the invention can be advantageously formed as a left foot section 100A, and a right foot section 100B, each of which can be depressed (i.e., be subject to vertical/"Z-axis" displacement as further described below) independently of the other section. Each of these sections 100A, 100B, is ideally comprised of a piece of planar rigid material (such as aluminum plate of suitable thickness) to avoid data errors and associated problems associated with plate flexure. Each such section 100A, 100B is also, in the preferred embodiments illustrated, supported at four points. These can be centered along the side edges of each such section and corresponding with the locations where the "Y axis" (front-to-back) and "X axis" (side-to-side) for each such plate section 100A, 100B, intersect the side of the section 100A, 100B. However, the same results are more simply and effectually achieved in the preferred embodiment by placement of said supports at the corners of sections 100A, 100B. The supports are comprised of pressure sensors 100C such that the weight borne by each said section 100A, 100B, is supported by and through its respective four pressure sensors 100C. (ELF pressure sensors of the type manufactured by TEKSCAN® can be suitably used for the pressure sensors of the invention). A simple voltage divider composed of off the shelf resistors can be utilized to obtain a signal from the said plurality of sensors 100C (which can suitably be TEKSCAN® FlexiForce sensors). The voltage divider can be easily tuned to adjust the range of the FlexiForce sensors as needed. The pressure sensors 100C are wired through an op-amp based circuit to normalize data for various weights. A National Instruments USB 6009 data acquisition device (DAQ) is used to convert the analog signal from the pressure sensors 5 to a 14-bit digital variable readable on a USB port. The DAQ can also provide the 5V power source for the FlexiForce sensors, eliminating the need for an external power supply.

The data processing subsystem 103 of the invention, which can conveniently utilize numerous forms of computer or other processing devices, relies on a software subsystem to process video data from the video processing system 101 to generate information on the subject's center of mass and/or core alignment, and to process force distribution data from the foot force analysis system 102 to generate information on distribution of subject weight at the subject's feet and/or a center of force at the subject's feet. It is responsible for extracting 2D coordinates for each target marker 301, 302, 303, 304, 305, 306, 307 on both cameras 103A, 103B, combining the coordinates into 3D, importing and normalizing data from sections 100A, 100B, running a feedback system from the measurements, and calculating a balance score from the provided data as well as analyzing balance deficits.

However, notwithstanding the many advantages over prior art embraced and included in the inventive concepts previously set forth, a problem remains: how to calibrate and quantify baselines for balance and (where working with the elderly, stroke victims and others with similar balance problems) likelihood of falling. Somewhat subjective measurements of balance in terms of likelihood of falling have been developed, such as the Berg Balance Scale. The Berg scale has the subject perform fourteen different activities with a score of 0-4 being given by a therapist for each activity based on how well balance is maintained during the activity. In general, using the Berg scale, a score of 0-20 indicates someone with very poor balance (fall risk high) who is, or should be, wheelchair bound; a score of 21-40 indicates someone with some balance (fall risk medium) who should be able to walk with assistance, and a score of 41-56 indicates someone with better balance (fall risk low) who should be able to move about independently. However, the Berg scale has not been subject to objective confirmation and includes subjective evaluation factors that make its reliability doubtful.

In addition, all methods for evaluating of measuring stability previously developed (as well as the systems of the instant invention) require the development of an objective scale against which the performance of (and data derived from) an individual can be compared and measured and calibrated. Measurement of large numbers of individuals can allow the eventual development of scales and standards in different areas that should be statistically accurate. However, problems arise using this methodology. First, the data scatter inevitable in seeking to establish standards in this fashion means that very large numbers of measurements must be taken in order to establish reliable standards. This is an unnecessary handicap in establishing and using the inventions described herein for measuring balance as a viable and reliable tool. Second, measurements taken in this way cannot be immediately correlated with likelihood of falling. The establishment of a statistically reliable bell curve in terms of overall balance is not an indicator—by itself—of likelihood of falling. Third, it is advantageous, especially when dealing with the elderly and infirm, to be able to measure balance and likelihood of falling without subjecting the subject to numerous test activities (in the manner of the Berg Balance Scale).

In view of the foregoing, a mechanical structure has been developed that has balance characteristics analogous to those of the human body when evaluated using the apparatus of the invention. This proved to be a complex task, but has been accomplished via the Balance Tester 600 invented, and illustrated in FIGS. 4A through 7. Turning first to the embodiment illustrated in FIGS. 4A, 5, 6 and 7, it will be seen that the Balance Tester 600 has a leg portion (indicated generally by arrow 601) supporting a torso portion (indicated generally by arrow 602). The leg portion 601 is subdivided into two legs 601A, each of which terminates at its lower end in a foot (or base member) 601B comprised of two brass rods (with indicated points of support/force F1, F2, F3, F4, F5, F6, F7, and F8). At its top end, each leg 601A is attached to a waist member (plate 603), which serves as a mount for a variable speed DC motor 604 and a movable motor counterweight 605. Motor 604 drives a disc 604A with eccentric holes 604B therein. A rod 606 can be connected between one of the said holes and one of the legs 601A. In this manner, motor 604 can be used to drive and induce lateral sway (with a predetermined speed and amplitude) to the system. (In this regard, it should also be noted that legs 601 are hingeably connected to plate 603 and the two base members 601B via bushed pins 606, which allow and permit such lateral sway).

Torso portion 602 is mounted to plate 603 so as to be adjustable for frontal/dorsal tilt and is adapted via its shape (having a central upright member 603A and upper/lower cross members 603B) for mounting/fastening of the adjustable vest 300 with motion capture targets 300A thereon in a manner analogous to that in which it would be worn by a human subject. It is also pivotal (i.e., axially rotatable around the vertical axis Z). In addition, torso portion 602 has a movable (frontal/dorsal) obesity simulation weight system 607 mounted thereto, which can be used to simulate the weight distribution of individual subjects, and is particularly useful in adapting the Balance Tester to provide results analogous to those produced by such subjects.

As will be appreciated, the foregoing design features allow the Balance Tester 600 to be mounted to the foot pads of the balance testing system of the invention and driven in different modes until a balance failure is reached (i.e., it falls forward, backward, or sideways) in order to determine the likelihood of falling (and stability) of humans producing analogous data when tested. Thus, by way of example, by setting various values/positions of obesity simulation weight system 607 and upright member 603A, with each base member 601B on a separate section 100A, 100B it can be driven for lateral sway. Likewise, by positioning the base members 601B across (or transverse to sections 100A, 100B) and rotating torso portion 602 to the front/back position (transverse to base members 601B), it can be driven for front/back sway. These tests can be performed at various frequencies and amplitudes by variable speed DC motor 204, allowing the precise criteria and data combinations at which balance failure is likely to occur to be determined. The Balance Tester 600 can be made more or less "obese" by moving the weight of obesity simulation weight system 607 in/out. (The embodiment in FIG. 4A varies the distribution of weights somewhat, using an upper obesity simulator 607A as well as a lower obesity simulator 607B, with these two being used both to counter the weight of motor 604 and to allow more flexibility in adjustment for upper body/lower body weight distribution as in for example, heavy upper chest/breast situations). Current draw of motor 604 is also measured to develop a power calculation. This system makes it possible to correlate the scoring software of the invention in terms of fall potential without the need for multiple human subjects. It is entirely measurable and repeatable in scientific terms to establish scores which indicate fall potential.

Figure 8:
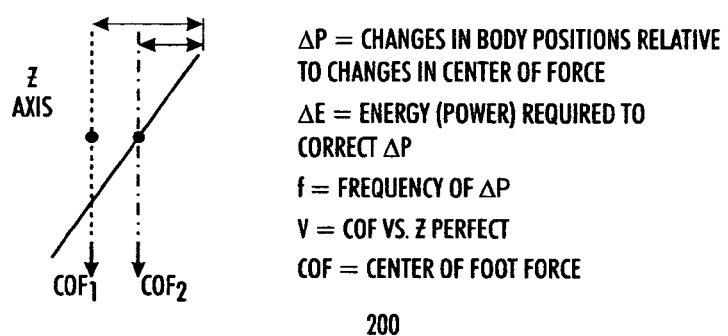
FIG. 8 schematically illustrates and sets forth some of the principle factors measured and analyzed by the system of the invention.

In keeping with the aforesaid system and in accordance with results received from said testing apparatus, a preferred mode for processing, evaluating, interpreting and/or scoring balance and performance data has been developed. This mode and system of the invention focuses upon direct measurement of the combinations of physical movements in the human body which are constantly being exerted to maintain balance and on the power required in that exertion. Once these measurements have been made they are rendered into a set of scores by use of mathematical treatment of vector analysis, using Fourier transforms and simultaneous differential equations. FIG. 8 schematically illustrates and sets forth some of the principle factors measured and analyzed (200), with others being discussed and further explicated below. As measured by foot force analysis subsystem 102, a first/earlier center of force measured $COF_1$ and a second/later center of force measured $COF_2$ represent the vectors of changes in the center of forces at the feet, since the center of force "COF" is constantly changing as a person sways front-back (X-axis) and laterally (Y-axis) and acts to maintain balance. As measured using video processing subsystem 101 (which gathers video data related to a subject's upper body position), ΔP represents the changes in upper body position in the three axes (X, Y, Z) which are measured concurrently. These vectors are scored both individually as well as together so that the therapist can determine relative contributions of feet and body core in maintaining balance, as well as determining an overall result of their combination. The latter is the most sensitive indicator of the subject's balance disposition and risk of fall.

Figure 9:
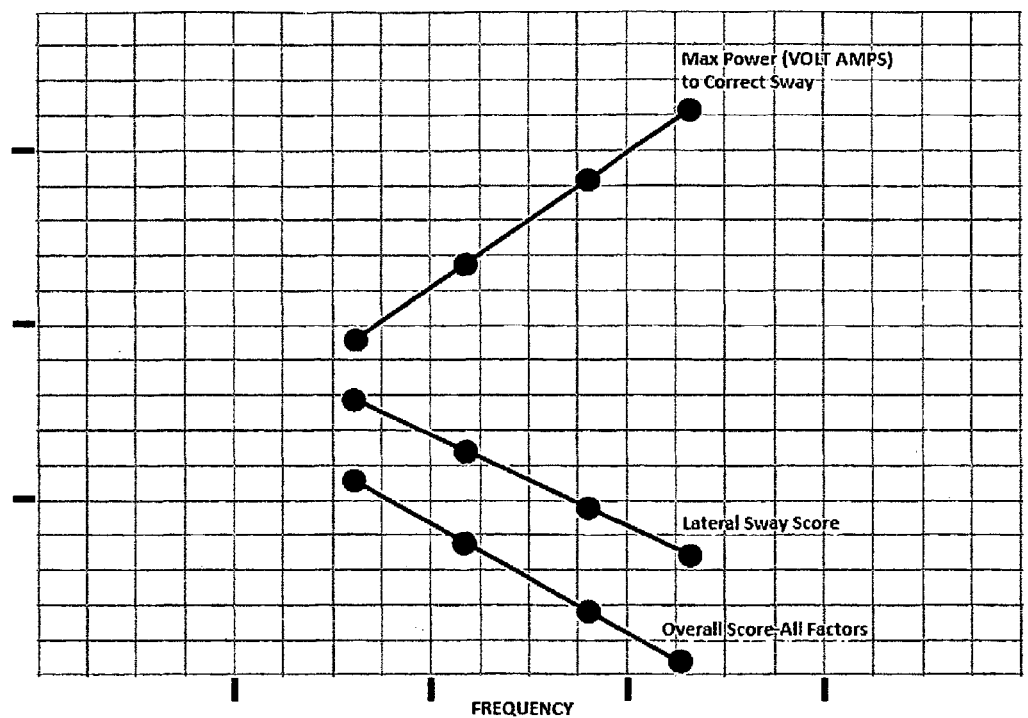
FIG. 9 provides a schematic graph illustrating the interrelationship of various factors related to balance as established via use of the Balance Testing Device of the invention.

Further measurements are made for even more extensive evaluation of the subject. The frequency of upper body sway is measured at each change in direction in the X and Y axes. Postural alignment (V) is measured vs. a perfect vertical to indicate whether the upper body is out of position (i.e. bent over) from the Z axis passing through the COF. Delta E indicates the energy (power) required to correct sway in the upper body and to change the COF. This Delta E measurement is correlated to the scores for frequency, sway and alignment through use of the Balance Tester previously discussed. FIG. 9 provides a schematic graph illustrating the interrelationship of various factors related to balance as established via use of the Balance Testing Device of the invention. A graph of this correlation is shown in FIG. 9 under various Delta P configurations of the device. As will be seen, power required to correct sway directly tracks and is inversely proportional to the intensity of sway and overall balance score.

The scoring software takes the measurement results of the Fourier analysis and automatically assigns a score of 100 as best. In arriving at and displaying the results derived from the preferred mode for processing, evaluating, interpreting, displaying and/or scoring balance and performance data, the sway score measures the variance of the 7 markers (300A) in each of the 3 movement planes—x, y and z. The variance is the square of the standard deviation. The alignment score measures the sum of the absolute distance each marker travels from its initial starting point in each of the 3 planes of movement—x, y, and z for each frame of data. To calculate an alignment score out of 100 the summation above is multiplied by a constant factor (0.002) and subtracted from 100. The overall score is the average of the above calculated sway and alignment scores:

$$\text{overall} = \frac{\text{sway} + \text{alignment}}{2}$$

This overall score is used as an indicator for a potential fall. In this regard, in accordance with the experiments performed with the invention, and particularly those utilizing the Balance Tester described above, it has been found that: Low fall risk: overall>=90; Medium fall risk: 80<=overall<90; and High fall risk: overall<70. The vertical score (x-plane) measures the difference between the C7 (304) and L5 (307) marker positions in the x-plane for each frame of data. (The absolute difference in distance between the two markers is summed, and the sum is then divided by the number of frames (N) to get an average distance per frame). The vertical score (y-plane) measures the difference between the C7 (304) and L5 (307) marker positions in the y-plane for each frame of data. (The absolute difference in distance between the two markers is summed, and the sum is then divided by the number of frames (N) to get an average distance per frame). The frequency (x-plane) measures the number of times the C7 marker (304) changes direction and travels at least 1 pixel in the x-plane. The frequency (y-plane) measures the number of times the C7 marker (304) changes direction and travels at least 1 pixel in the y-plane. Finally, the average footpad % calculated the percentage of total force seen on the left and right foot throughout the duration of the test.

Figure 10:
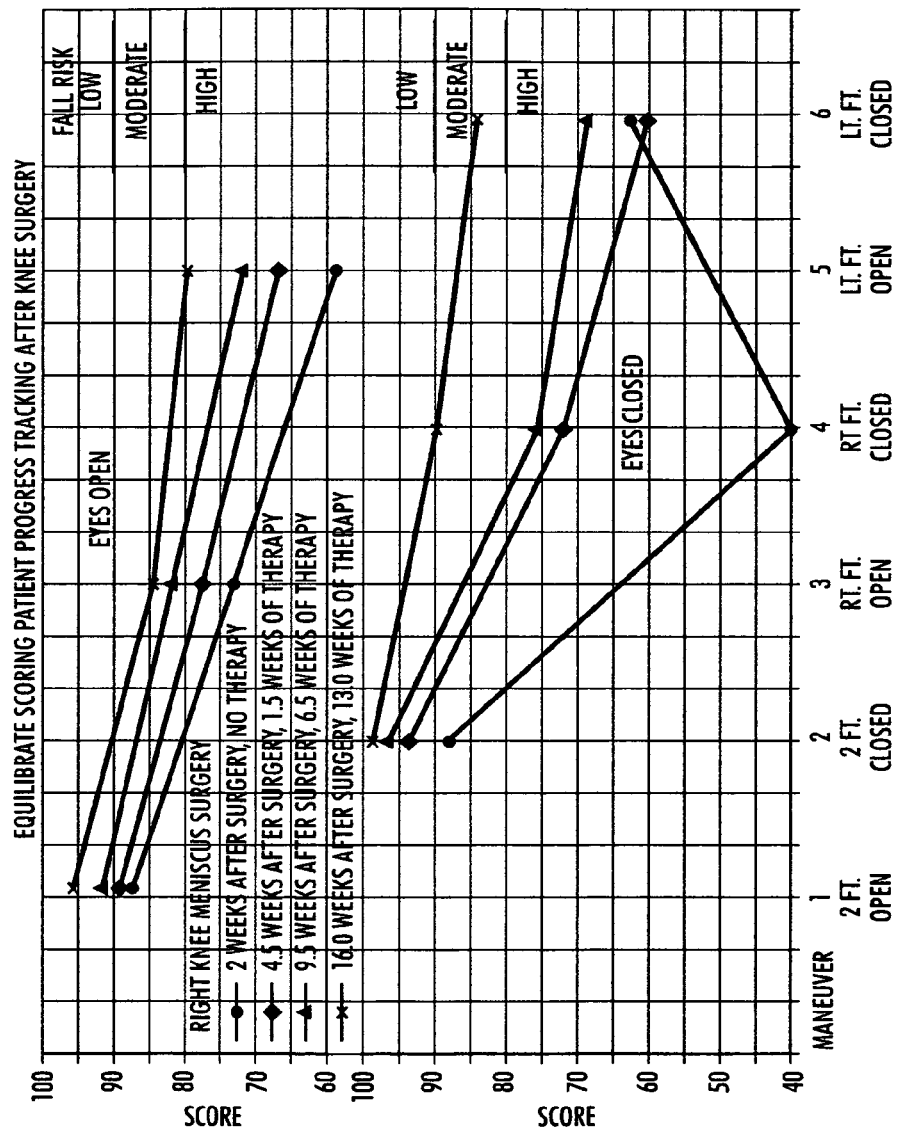
FIG. 10 provides graphs illustrating the scoring of a patient over a period of time using the apparatus of, and in accordance with the system of the invention.
Figure 11:
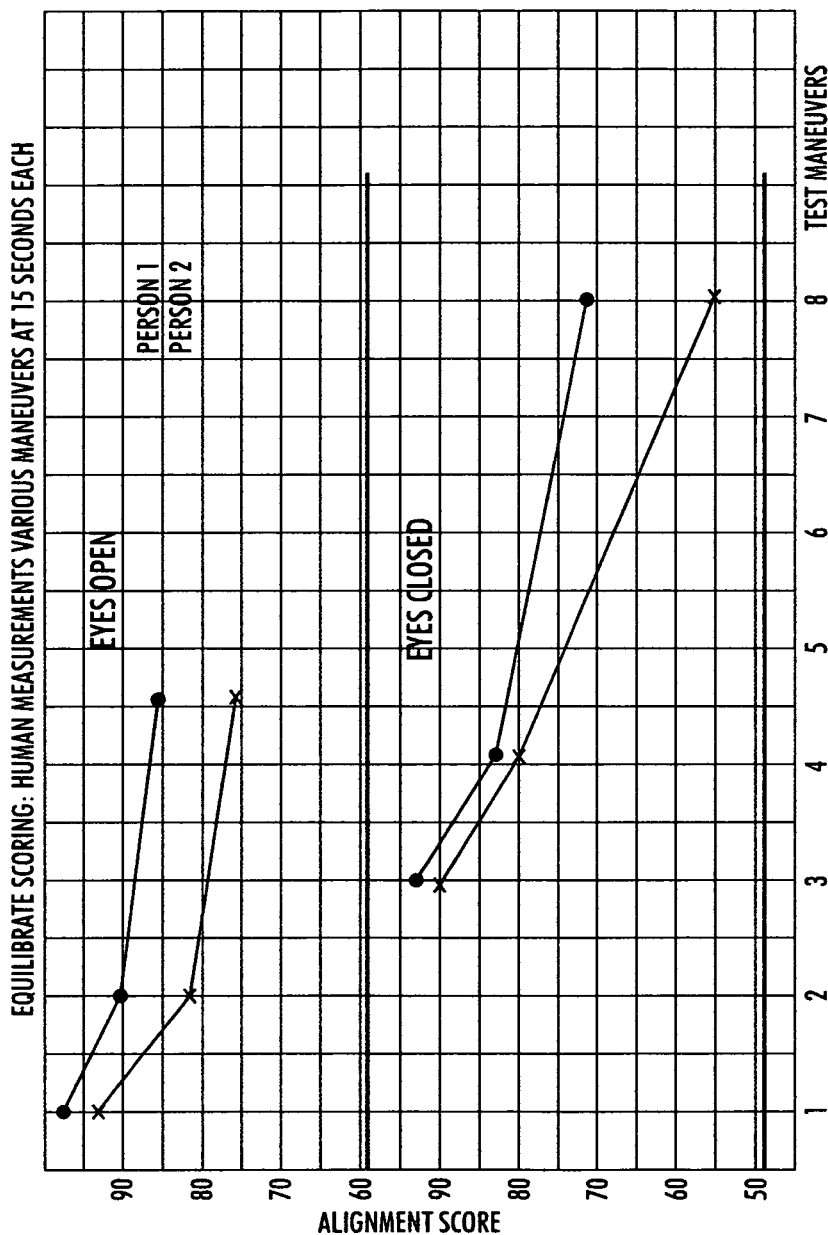
FIG. 11 provides graphs illustrating the scoring for two separate subjects measured at the same time.

FIG. 10 provides graphs illustrating the scoring of a patient over a period of time using the apparatus of, and in accordance with the system of the invention, showing the improvements seen by patient and therapist over a period of time after knee surgery while performing certain set maneuvers (i.e., balancing on both feet with eyes open and closed, balancing on right foot with eyes open and closed, and balancing or left foot with eyes open and closed). FIG. 11, on the other hand, provides graphs illustrating the scoring for two separate subjects measured at the same time using the same testing regimen. As will be noted, both of these figures both illustrate and confirm the efficacy of the invention in tracking both improvement of balance over a period of time, individual differences in balance, and the relative difficulties of various maneuvers and situations imposed in terms of maintaining balance.

Figure 12:
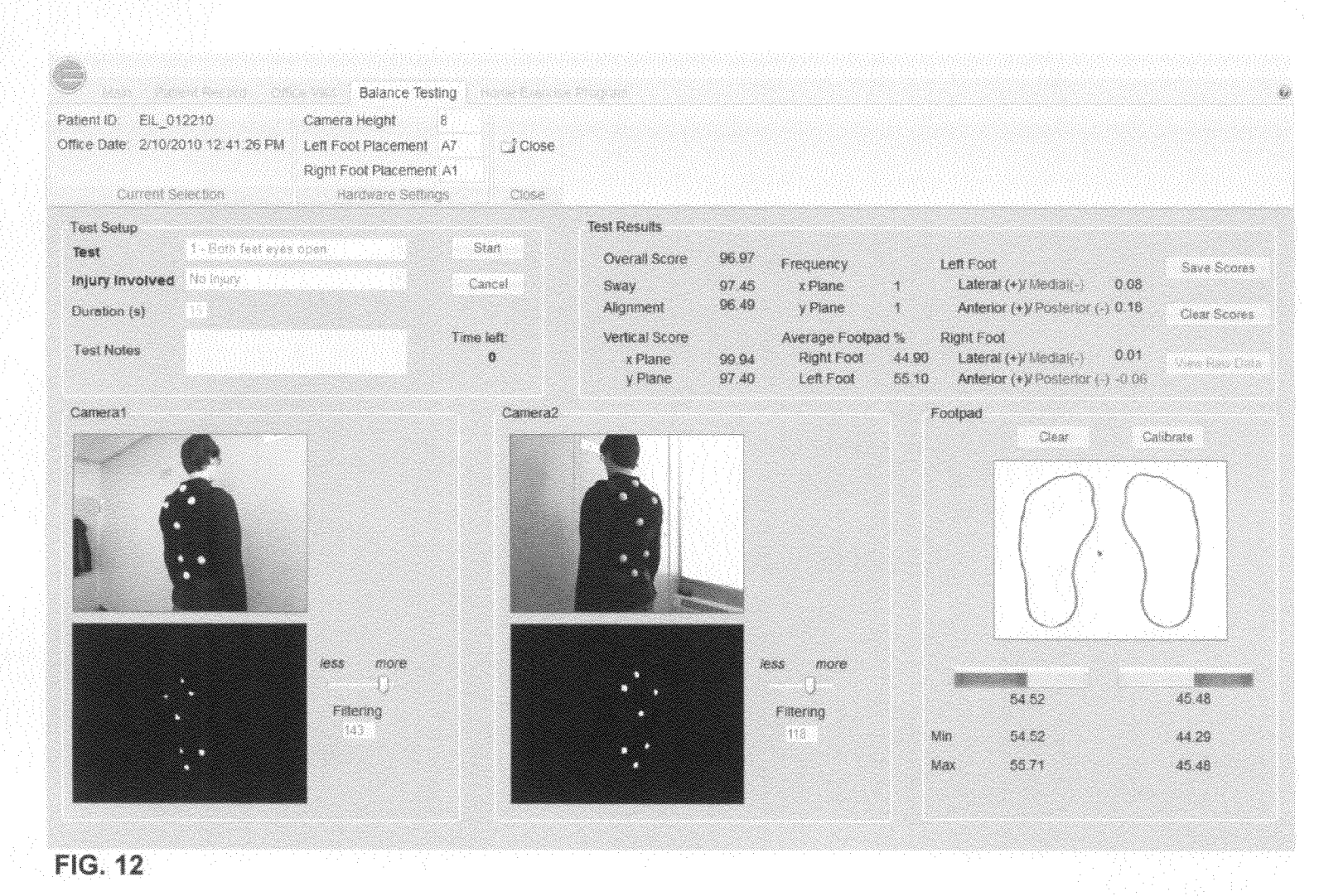
Figure 13:
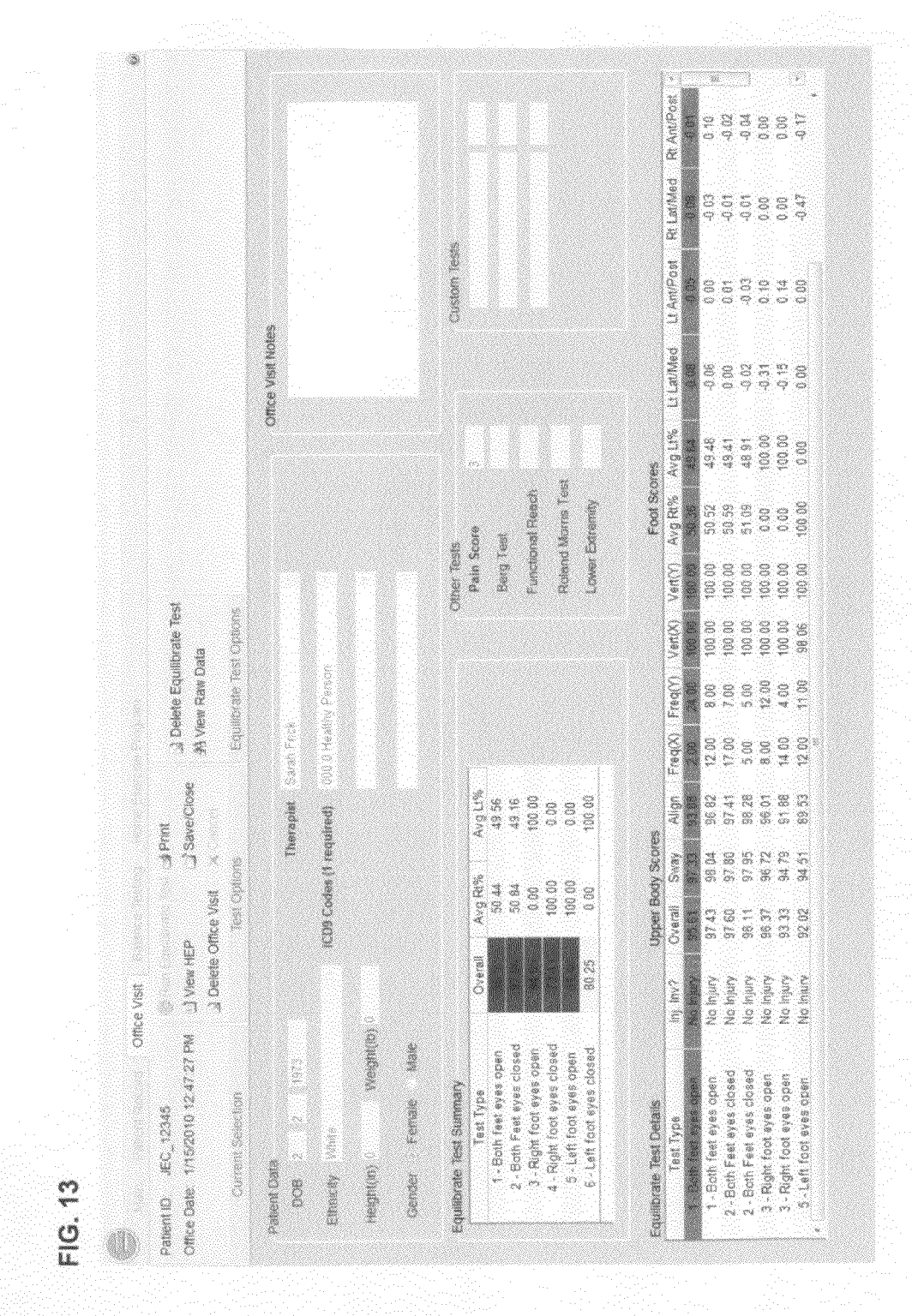
Figure 14:
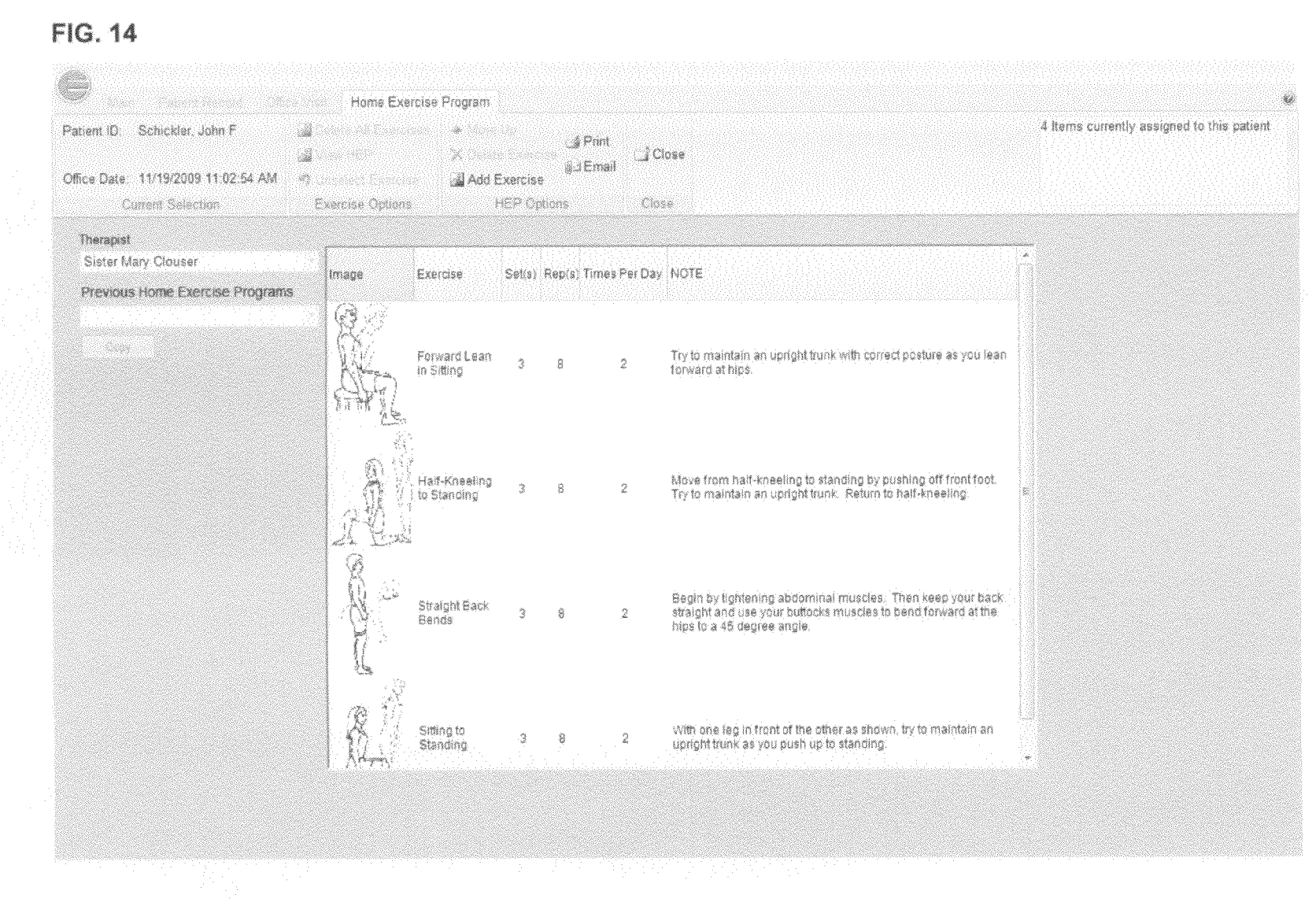
Figure 15:
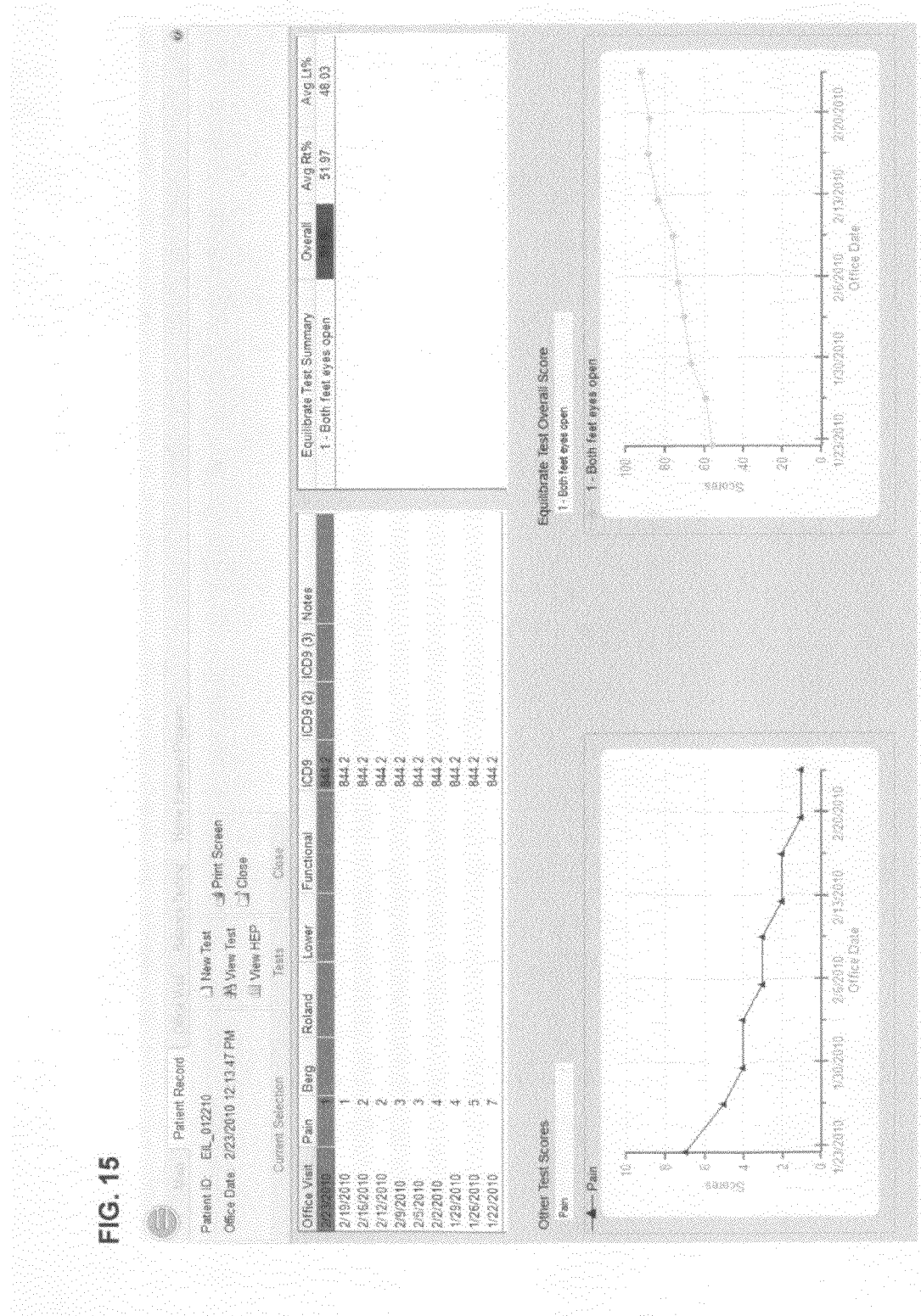
FIG. 15 is a fourth exemplary screen shot provided in accordance with the teaching and system of the invention, illustrating a record of patient history which is automatically calculated and stored in the software.

FIGS. 12 through 15 provide exemplary screen shots illustrating many of the features and benefits of the feedback subsystem 104 of the invention. FIG. 12 is a first exemplary screen shot provided in accordance with the teaching and system of the invention, providing output based on the scoring and measurement system described above, as well as illustrating individual foot forces, live feed from the video processing subsystem 101, and displaying upper body movement via video capture of the luminous pods 300A on the hack of a vest 300 worn by the subject. FIG. 12 shows that the therapist can see the capture of each pod 300A. Every slightest movement of every pod 300A is captured and recorded and can be analyzed by the therapist. The pod 300A movement is automatically scored in the software, as explained above. FIG. 13 illustrates the patient record which is automatically stored for reference by both patient and therapist. In FIG. 13, the color codes indicate risk of fall (green low, yellow moderate, red high). On this screen, test types 1-3 and 5 are indicated as green, while test type 6 is yellow and test type 4 is red (indicating a high risk of falling under these conditions). This screen can be copied and emailed to the patient. FIG. 14 illustrates the selection of various therapeutic protocols from a library stored in the software and customized by the therapist as a result of reviewing the scoring in FIG. 13. These protocols are recorded and stored for each patient and can be copied and emailed to the patient. Every patient record is protected in the software. FIG. 15 is a fourth exemplary screen shot provided in accordance with the teaching and system of the invention, illustrating a record of patient history which is automatically calculated and stored in the software. FIG. 15 illustrates a record of patient history which is automatically calculated and stored in the software.

Figure 16:
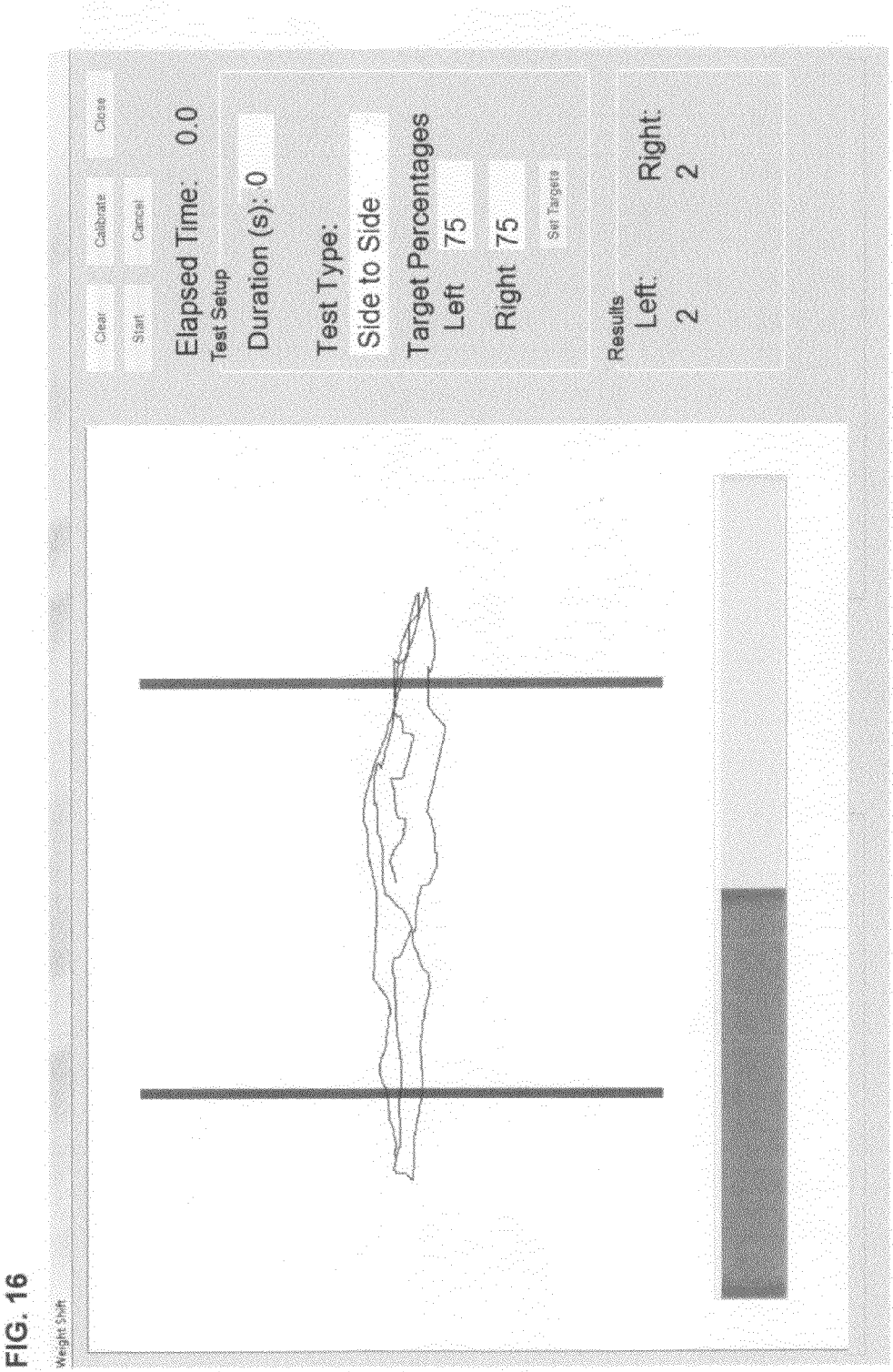
FIG. 16 is a fifth exemplary screen shot provided in accordance with the teaching and system of the invention, illustrating screen results of a first balance measurement and improvement exercise.
Figure 17:
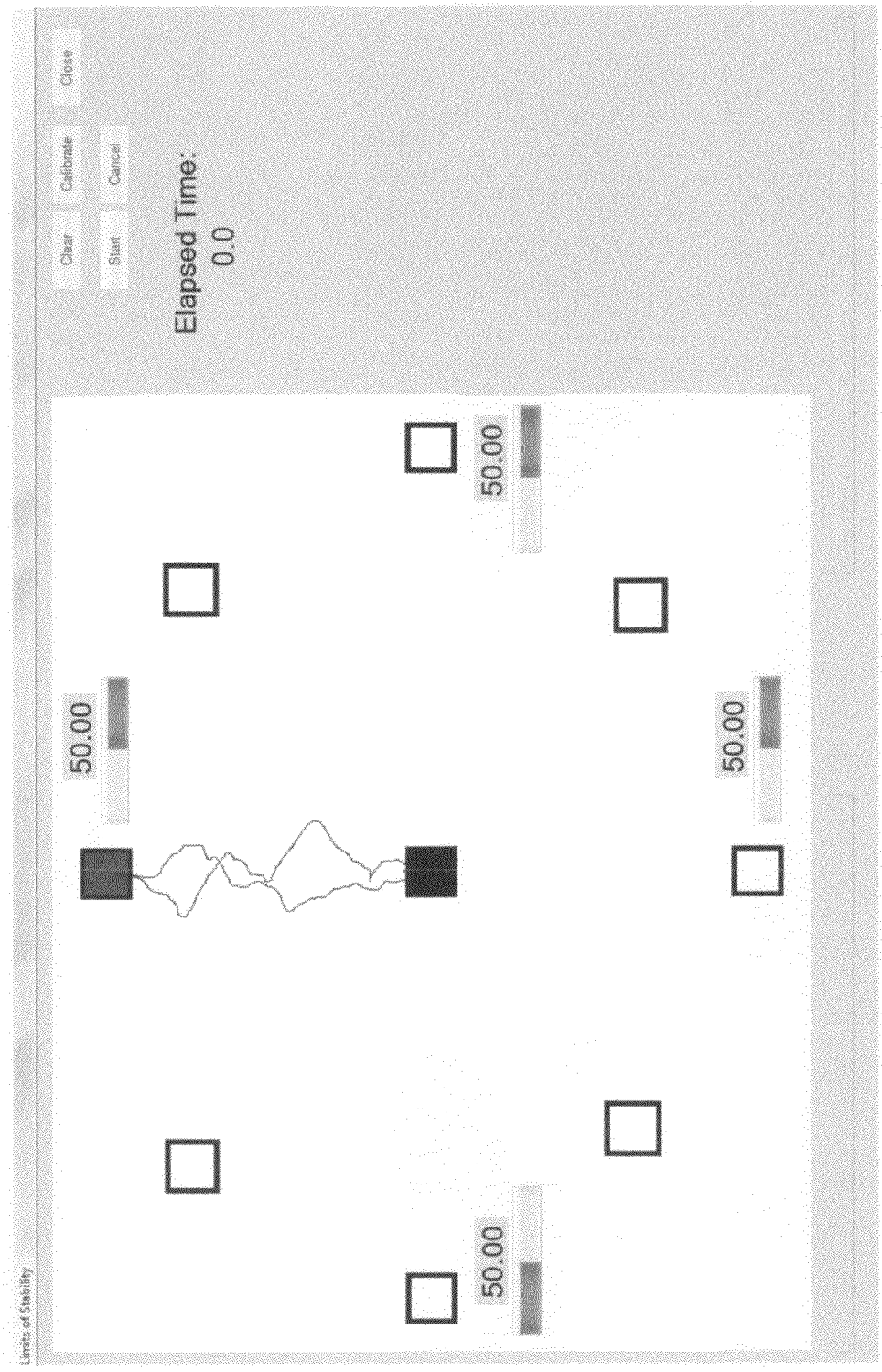
FIG. 17 is a sixth exemplary screen shot provided in accordance with the teaching and system of the invention, illustrating partial results of second balance measurement and improvement exercise.
Figure 18:
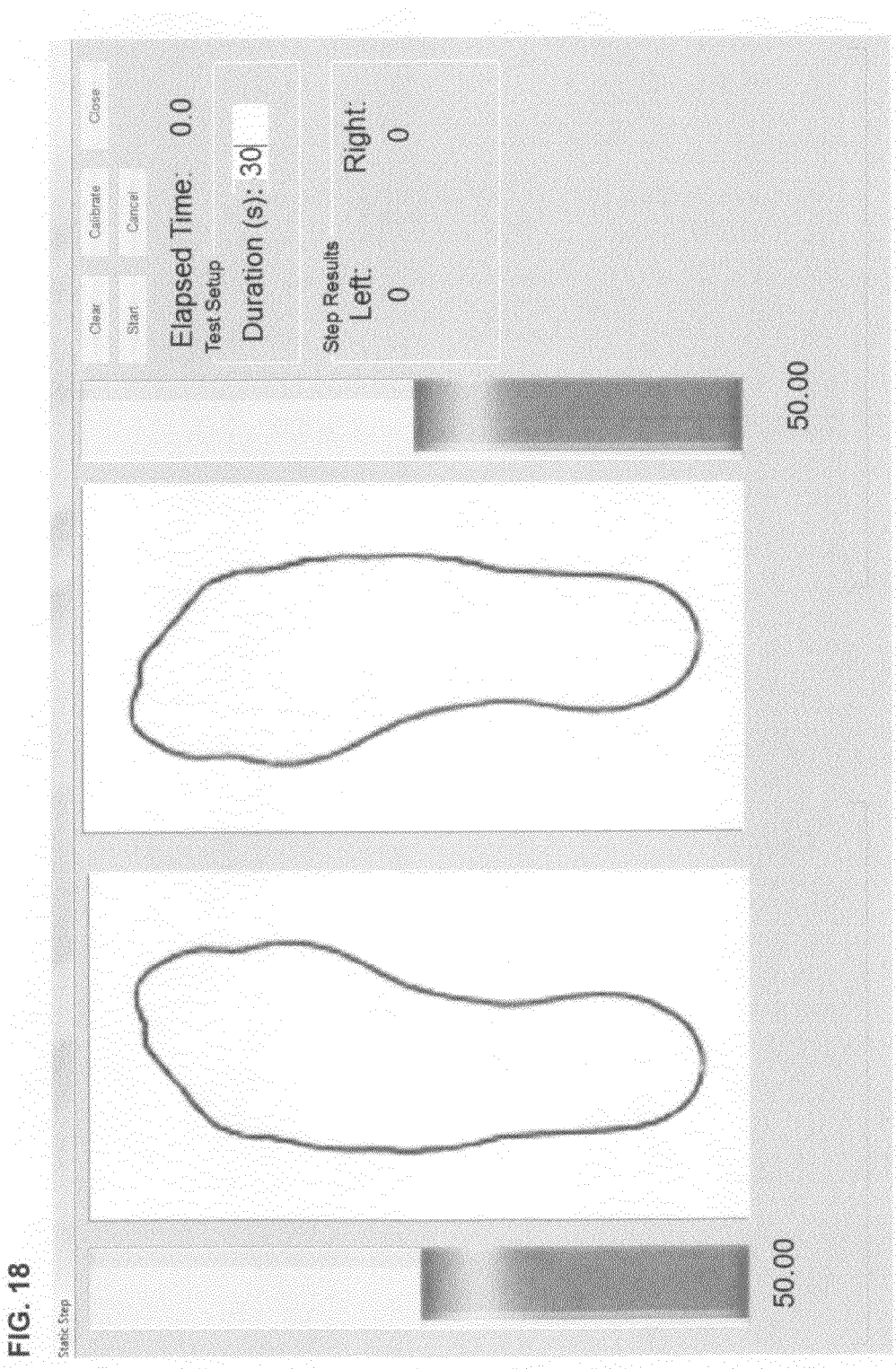
FIG. 18 is a seventh exemplary screen shot provided in accordance with the teaching and system of the invention, illustrating a third balance measurement and improvement exercise.
Figure 19:
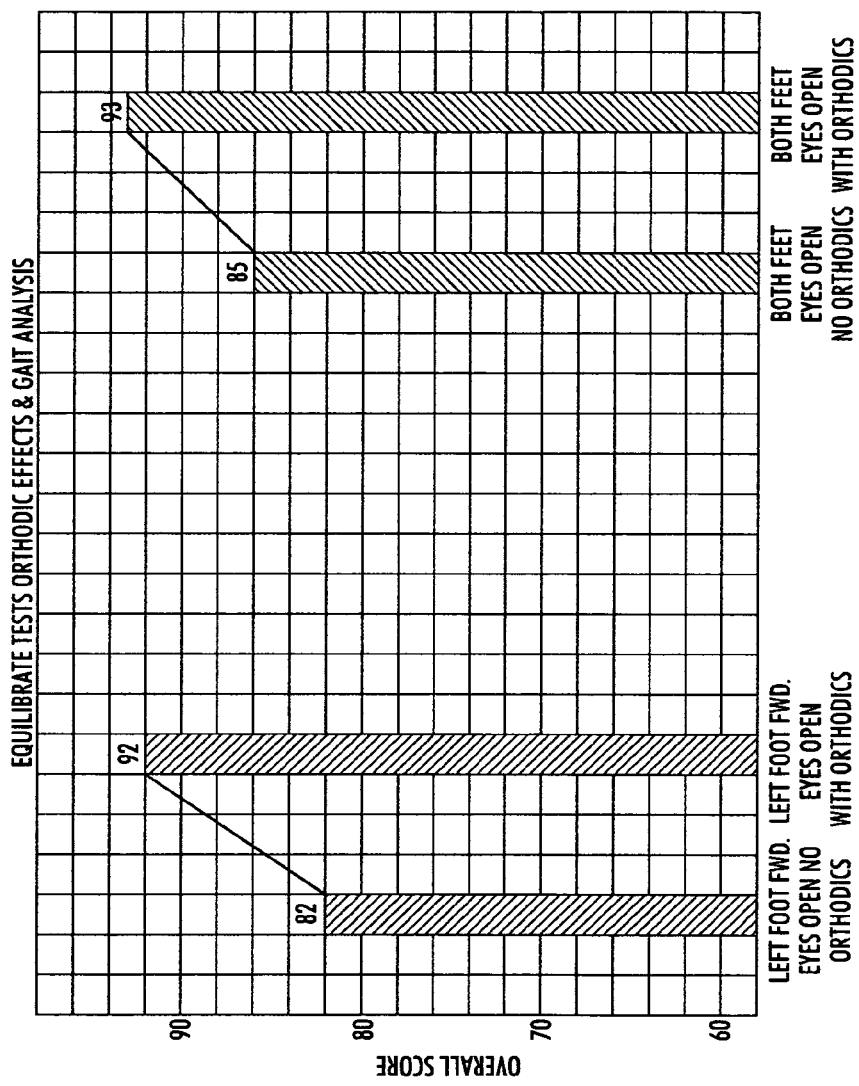
FIG. 19 provides a graph illustrating the balance improvements enjoyed by a patient wearing suitable orthotics as measured by the invention.

Finally, as shown in FIGS. 16, 17, and 18, the software includes provision for therapeutic exercises that are performed on the equipment. These are chosen by the therapist based upon the scores defined in FIG. 13. The patient watches these screens while performing the exercises and can review previous results to see a chart of progress. FIG. 16 shows screen results of a balance measurement and improvement exercise where the subject sways/leans (e.g., from side-to-side) while attempting to maintain balance. The sway is measured between the two vertical lines (which are preset as a goal), with the patients repetitive movements back-and-forth illustrated by the lines between. FIG. 17 illustrates a similar exercise, but one performed between preset markers along eight points around the patient, such that the patient is forced to accomplish a forced lean (while maintaining balance) to the front, the right front corner, the right side, the right back corner, the back, the left back corner, the left side, the left front corner, and back in such order and sequence as may be determined by the therapist. FIG. 18 provides an exemplary screen shot illustrating another balance measurement and improvement exercise, where the patient strives to maintain perfect center of force (COF) and/or other exercises based on prescribed movement of COF in a regime determined by the therapist.

As the patient and therapist utilize the resources provided by the invention, balance improves as the variation from the center of alignment improves, primarily achieved by strengthening the body core and improving its alignment. Variations are measured over time in order to assure and measure stability. The result is an integration of three components of posture, sway and support into one balance actualization and measurement system using appropriate software and display apparatus to process and display data and other information derived from the aforesaid sources. Experiments have shown that the core alignment factor is of critical importance in measuring and improving balance. Therefore, as a result of this invention, human balance can now—finally—be scientifically and effectively defined as: A state of stability in maintaining parallel alignment of the vertical axis of the body core with the vertical axis of the center of force at the points of support of the entire body.

However, numerous variations are possible without deviating from and/or exceeding the spirit and scope of the invention. Thus, as the foregoing makes clear, the invention generally comprehends all systems for a human balance analysis and improvement apparatus and method that involve the use of separate and synergistically integrated and combined means for analyzing and producing perfect core body alignment and balance: a torso alignment indicator and sway measurement apparatus and system, a foot force measurement and force centering apparatus and system, balance information display apparatus and system, processing apparatus and systems for combining and facilitating the operations of the foregoing and/or apparatus for calibration of the balance measurement devices and systems described in order to arrive at objective standards and measurements for balance and likelihood of falling. In addition, as the foregoing should also make clear, numerous variations can be made without exceeding the inventive concept. Moreover, many of the above-disclosed and other features and functions, or alternatives thereof, may be desirably combined into many other different systems Of applications. Also, various presently unforeseen or unanticipated alternatives, modifications, variations or improvements therein may be subsequently made by those skilled in the art which are also intended to be encompassed by the claims to be filed hereafter.

What is claimed is:

1. A human balance analysis and improvement method, comprising:
    providing an information processing and display system including a data processing subsystem and a feedback subsystem, where the data processing subsystem is in electronic communication with a stationary foot force analysis pad and a torso position measurement apparatus positioned such that a subject standing on said foot force analysis pad is positioned to have the subject's torso position measured by said torso position measurement apparatus;
    positioning a standing subject on said foot force analysis pad so that the foot force analysis pad electronically communicates information on the distribution of force exerted on said pad by the subject standing thereon to said data processing subsystem and the torso position measurement apparatus electronically communicates information on position of the subject's torso while standing on said pad to said data processing subsystem;
    processing the information electronically communicated by at least one of said pad and said torso position measurement apparatus via the data processing subsystem of said information processing and display system, said processing including vector analysis using Fourier transforms and simultaneous differential equations; and
    displaying information via the feedback subsystem of said information processing and display system so as to assist at least one of the subject and a therapist to at least one of: determine and maintain subject bodily alignment and balance while standing on said pad, perform subject exercises to assist the subject in developing bodily alignment and balance while standing on said pad, track bodily alignment and balance while performing certain subject maneuvers while standing on said pad, and track changes in subject bodily alignment and balance over a period of time while standing on said pad.

2. The human balance analysis and improvement method of claim 1, wherein at least one of:
    said pad and has at least two rigid side-by-side sections capable of independent movement with respect to each other with each of said sections being in communication with a plurality of force sensors such that forces exerted on said section will be detected by said sensors, and wherein said pad electronically communicates information on the distribution of force exerted on said pad by the subject standing thereon to said data processing subsystem,
    said pad and has at least two rigid side-by-side sections capable of independent movement with respect to each other with each of said sections being in communication with a plurality of force sensors such that forces exerted on said section will be detected by said sensors, wherein said pad electronically communicates information on the distribution of force exerted on said pad by the subject standing thereon to said data processing subsystem, and wherein said information processing and display system displays a center of force based on force information received from said sensors,
    said torso position measurement apparatus comprises video capture targets positioned on a vest for wear by the subject with a video camera focused thereon,
    said information processing and display system indicates a center of force for the subject's weight based on force information received from said pad,
    said information processing and display system indicates postural alignment based on force information received from said pad,
    said information processing and display system indicates alignment of the subject's torso with the center of force for the subject's weight,
    said information processing and display system provides a sway score,
    said information processing and display system provides an alignment score, and
    said information processing and display system provides an overall balance score based on a sway score and an alignment score.

3. The human balance analysis and improvement method of claim 2, wherein said information processing and display system provides a sway score measuring the variance of each target in x, y, and z planes.

4. The human balance analysis and improvement method of claim 3, wherein said variance is the square of the standard deviation.

5. The human balance analysis and improvement method of claim 4, wherein said information processing and display system provides an overall balance score by averaging the sway score and alignment score.

6. The human balance analysis and improvement method of claim 5, wherein said information processing and display system provides an alignment score.

7. The human balance analysis and improvement method of claim 3, wherein said information processing and display system provides an overall balance score by averaging the sway score and alignment score.

8. The human balance analysis and improvement method of claim 2, wherein said information processing and display system provides an alignment score measuring the sum of the absolute distance each target travels from its initial starting point in x, y, and z planes.

9. The human balance analysis and improvement method of claim 8, wherein to calculate an alignment score out of a possible top score the summation above is multiplied by a constant factor and subtracted from the possible top score.

10. The human balance analysis and improvement method of claim 8, wherein said information processing and display system provides an overall balance score by averaging the sway score and alignment score.

11. The human balance analysis and improvement method of claim 10, wherein said information processing and display system provides an overall balance score based on a sway score and an alignment score.

12. The human balance analysis and improvement method of claim 2, wherein said information processing and display system provides an overall balance score by averaging the sway score and alignment score.

13. A human balance analysis and improvement method, comprising:
- providing an information processing and display system including a data processing subsystem and a feedback subsystem, where the data processing subsystem is in electronic communication with a stationary foot force analysis pad and a torso position measurement apparatus positioned such that a subject standing on said foot force analysis pad is positioned to have the subject's torso position measured by said torso position measurement apparatus;
- positioning a standing subject on said foot force analysis pad so that the foot force analysis pad electronically communicates information on the distribution of force exerted on said pad by the subject standing thereon to said data processing subsystem and the torso position measurement apparatus electronically communicates information on position of the subject's torso while standing on said pad to said data processing subsystem;
- processing the information electronically communicated by at least one of said pad and said torso position measurement apparatus via the data processing subsystem of said information processing and display system;
- displaying information via the feedback subsystem of said information processing and display system so as to assist at least one of the subject and a therapist to at least one of: determine and maintain subject bodily alignment and balance while standing on said pad, perform subject exercises to assist the subject in developing bodily alignment and balance while standing on said pad, track bodily alignment and balance while performing certain subject maneuvers while standing on said pad and track changes in subject bodily alignment and balance over a period of time while standing on said pad; and wherein the human balance analysis and improvement apparatus is calibrated using a balance testing device.

14. The human balance analysis and improvement method of claim 13, wherein said pad and has at least two rigid side-by-side sections capable of independent movement with respect to each other with each of said sections being in communication with a plurality of force sensors such that forces exerted on said section will be detected by said sensors, and wherein said pad electronically communicates information on the distribution of force exerted on said by the subject standing thereon to said data processing subsystem.

15. The human balance analysis and improvement method of claim 13, wherein said information processing and display system displays a center of force based on force information received from said sensors.

16. The human balance analysis and improvement method of claim 13, wherein said torso position measurement apparatus comprises video capture targets positioned on a vest for wear by the subject with a video camera focused thereon.

17. The human balance analysis and improvement method of claim 13, wherein said information processing and display system indicates a center of force for the subject's weight based on force information received from said pad.

18. The human balance analysis and improvement method of claim 13, wherein said information processing and display system indicates postural alignment based on force information received from said pad.

19. The human balance analysis and improvement method of claim 13, wherein said information processing and display system indicates alignment of the subject's torso with the center of force for the subject's weight.

20. The human balance analysis and improvement method of claim 13, wherein said information processing and display system provides a sway score.

* * * * *